United States Patent
Hou et al.

(10) Patent No.: US 9,839,782 B2
(45) Date of Patent: Dec. 12, 2017

(54) SYSTEMS FOR, AND METHODS OF, GUIDANCE BASED INTRAOPERATIVE CARDIAC RESYNCHRONIZATION THERAPY OPTIMIZATION

(71) Applicant: PACESETTER, INC., Sylmar, CA (US)

(72) Inventors: Wenbo Hou, Santa Clarita, CA (US); Craig D. Markovitz, Jefferson Hills, PA (US); Chunlan Jiang, Crystal, MN (US); Stuart Rosenberg, Castaic, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 15/141,065

(22) Filed: Apr. 28, 2016

(65) Prior Publication Data

US 2017/0312524 A1 Nov. 2, 2017

(51) Int. Cl.
*A61N 1/368* (2006.01)
*A61B 5/06* (2006.01)
*A61N 1/05* (2006.01)

(52) U.S. Cl.
CPC ............ *A61N 1/3688* (2013.01); *A61B 5/062* (2013.01); *A61N 1/056* (2013.01); *A61N 1/3682* (2013.01); *A61N 2001/0585* (2013.01)

(58) Field of Classification Search
CPC .. A61N 1/3627; A61N 1/3684; A61B 5/1107; A61B 2034/2046; A61B 2034/2051
See application file for complete search history.

(56) References Cited

U.S. PATENT DOCUMENTS

| | | | |
|---|---|---|---|
| 6,233,476 B1 | 5/2001 | Strommer et al. | |
| 7,343,195 B2 | 3/2008 | Strommer et al. | |
| 7,386,339 B2 | 6/2008 | Strommer et al. | |
| 7,778,688 B2 | 8/2010 | Strommer et al. | |
| 8,442,618 B2 | 5/2013 | Strommer et al. | |
| 2009/0157136 A1* | 6/2009 | Yang | A61B 5/0422 607/17 |
| 2012/0172867 A1* | 7/2012 | Ryu | A61B 18/1206 606/41 |

* cited by examiner

*Primary Examiner* — Allen Porter, Jr.

(57) ABSTRACT

The present disclosure may take the form of a method of optimizing CRT wherein candidate pacing settings are administered at a candidate lead implantation site. Such a method may comprise: determining a navigation sensor path at a measurement site for each candidate pacing setting at the candidate lead implantation site; and identifying which navigation sensor path corresponds to a most efficient cardiac tissue displacement.

14 Claims, 15 Drawing Sheets

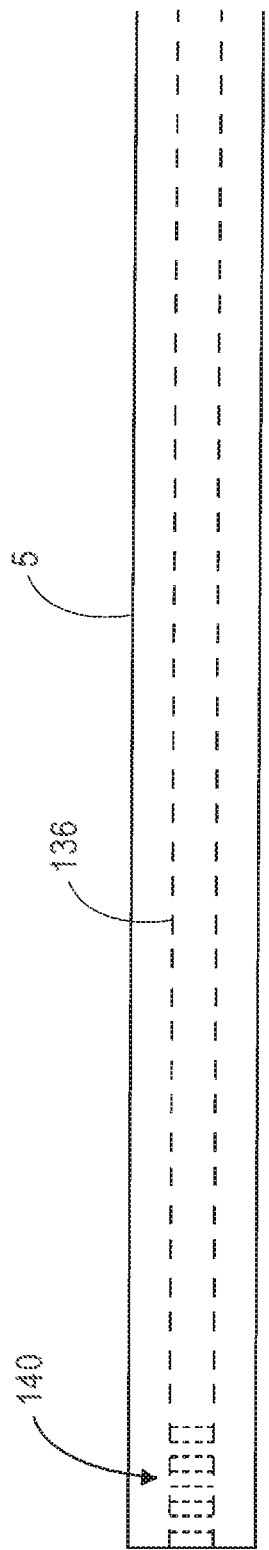
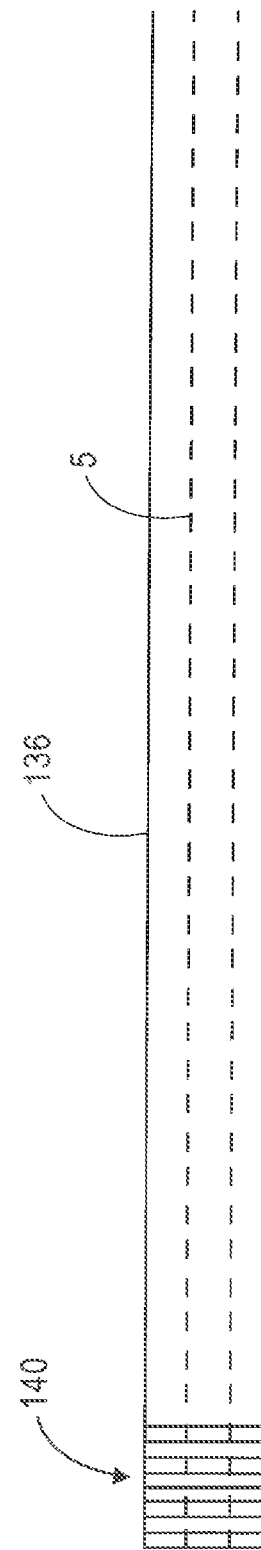

INEFFICIENT CONTRACTION: $E_{cc} \approx 0.0$

INEFFICIENT CONTRACTION: $E_{cc} \approx 1.0$

INEFFICIENT CONTRACTION:

$H_1 \approx \frac{\pi}{4}$, $H_2 \approx 1.0$ or $H_2 < 1$

INEFFICIENT CONTRACTION:

$H_1 \ll \frac{\pi}{4}$ $H_2 \gg 1$

SYSTEMS FOR, AND METHODS OF, GUIDANCE BASED INTRAOPERATIVE CARDIAC RESYNCHRONIZATION THERAPY OPTIMIZATION

FIELD OF THE INVENTION

Aspects of the present invention relate to medical apparatus and methods. More specifically, the present invention relates to systems for, and methods of, optimizing cardiac resynchronization therapy.

BACKGROUND OF THE INVENTION

Cardiac resynchronization therapy ("CRT") is a proven treatment for patients with heart failure and arrhythmia. The benefits of CRT are highly dependent on proper placement of the left ventricular ("LV") lead within the coronary sinus ("CS") or one of its branches.

There is a need in the art for systems for, and methods of, intraoperative optimization of LV lead placement associated with CRT.

BRIEF SUMMARY OF THE INVENTION

An embodiment of the present disclosure may take the form of a method of optimizing CRT wherein candidate pacing settings are administered at a candidate lead implantation site. Such a method may include: determining a navigation or medical positioning system (MPS) sensor path at a measurement site for each candidate pacing setting at the candidate lead implantation site; and identifying which MPS sensor path corresponds to a most efficient cardiac tissue displacement.

The method may further include programming an implantable pulse generator to administer electrotherapy to the candidate lead implantation site corresponding to the identified MPS sensor path and according to a candidate pacing setting corresponding to the identified MPS sensor path. Examples of candidate pacing settings include AAI, DDD, and VVI. The candidate pacing settings can be administered with different AVD.

Data associated with the MPS sensor path for each candidate pacing setting at the candidate lead implantation site can be normalized. Such normalization may be done by comparison to a baseline candidate pacing setting. The baseline candidate pacing setting may be AAI.

The determined MPS sensor paths may be analyzed regarding eccentricity. In one embodiment, the eccentricity of the identified MPS sensor path will be closer to a value of one than an eccentricity of any other of the determined MPS sensor paths.

The determined MPS sensor paths may be analyzed regarding hysteresis. In one embodiment, a first hysteresis component of the identified MPS sensor path will be less than a value of $\pi/2$ and also less than a first hysteresis component of any other of the determined MPS sensor paths. The first hysteresis component can be an area divided by a longest motion vector of a determined MPS sensor path, the area being enclosed by a total circumference of trajectory of the determined MPS sensor path.

In one embodiment, a second hysteresis component of the identified MPS sensor path is greater than a value of one and also greater than a second hysteresis component of any other of the determined MPS sensor paths. The second hysteresis component may be a diastolic portion of an area divided by a systolic portion of the area, the area being enclosed by a total circumference of trajectory of a determined MPS sensor path. In one embodiment, the MPS sensor path is tracked via a MPS sensor located in a low-power magnetic field, the MPS sensor employing a coil.

In one embodiment, the candidate lead implantation site is associated with a LV, and each candidate pacing setting is associated with LV pacing.

Another embodiment of the present disclosure may take the form of a system for optimizing CRT when candidate pacing settings are administered at a candidate lead implantation site in a portion of a patient heart. For example, the system may include a device, a tracking system and a processor. The device may include an MPS sensor at a distal end of the device, and the device may be configured to be delivered intravascular to the portion of the patient heart. The tracking system may be configured to record x-y-z positions of the MPS sensor in a three dimensional x-y-z coordinate system during administration of candidate pacing settings at the candidate lead implantation site. The processor may determine from the recorded x-y-z positions an MPS sensor path for each candidate pacing setting at the candidate lead implantation site. The system may also include a display that depicts the MPS sensor path. The processor may determine which MPS sensor path corresponds to a most efficient cardiac tissue displacement.

In one embodiment, the candidate pacing settings may include at least one of AAI, DDD, or VVI. The processor may normalize data associated with the MPS sensor path. For example, the data may be normalized by comparison to a baseline candidate pacing setting. The baseline candidate pacing setting may include AAI.

The processor may analyze the MPS sensor path regarding eccentricity. The processor may analyze the MPS sensor path regarding hysteresis.

The tracking system may include a low-power magnetic field, and the MPS sensor may include a coil that is tracked in the low-power magnetic field via the tracking system.

In one embodiment, the candidate lead implantation site is associated with a LV, and each candidate pacing setting is associated with LV pacing.

The device may include a stylet, guidewire, catheter, sheath or introducer. The device may include an implantable lead.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIG. 4A is a side view of distal region of the combination of the delivery tool and the LV lead, wherein the delivery tool is a guidewire, stylet, or other tool style configured to extend through the LV lead.

FIG. 4B is a side view of distal region of the combination of the delivery tool and the LV lead, wherein the delivery tool is a sheath, catheter, introducer or other tubular tool style configured to extend about the LV lead.

DETAILED DESCRIPTION

Implementations of the present disclosure involve systems for, and methods of, intraoperative optimization of left ventricular ("LV") lead placement associated with cardiac resynchronization therapy ("CRT"). Specifically, a navigation or medical positioning system (MPS) such as, for example, the St. Jude Medical MediGuide™ cardiovascular navigation system, is utilized to track the displacement of one or more navigation or MPS enabled sensors supported on the distal end of a lead delivery tool.

The St. Jude Medical MediGuide™ cardiovascular navigation system is a 3-D electromagnetic navigation system that provides real-time position and orientation of one or more MPS enabled sensors embedded in electrophysiological tools, including lead delivery tools. The St. Jude Medical MediGuide™ cardiovascular navigation system is integrated with a fluoroscopic imaging system and tracks the one or more sensors continuously within the imaging volume of the fluoroscopic system, on both live fluoroscopy and pre-recorded background.

As disclosed herein, a LV lead is placed at a candidate implantation site and administers electrotherapy to the candidate implantation site according to different candidate pacing settings. Meanwhile, one or more MPS enabled sensors are placed at different measurement sites in and around the coronary sinus ("CS") and the displacement of the MPS enabled sensors is tracked during periods of natural heart actuation and periods of heart actuation brought about by various forms of electrotherapy administered according to the different candidate pacing settings at the candidate implantation site. Algorithmic assessment of the displacement of the MPS enabled sensors identifies the implantation site and the electrotherapy resulting in the most efficient heart actuation, thereby optimizing the associated CRT. In other words, in one embodiment, the optimal pacing site and optimized programming settings during a CRT implant may be associated with the path of the MPS enabled sensor that is assessed to pertain to the most efficient heart displacement.

Before discussing in detail the algorithmic assessment of the path of an MPS enabled sensor to optimize lead placement and CRT settings, a general overview of CRT will first be provided, followed by a general discussion of an example MPS system, MPS enabled delivery tools, and candidate CRT lead implantation sites and measurement sites associated with the CS 21.

a. Overview of CRT, MPS Systems and Tools, and CS Structure

Figure 1:
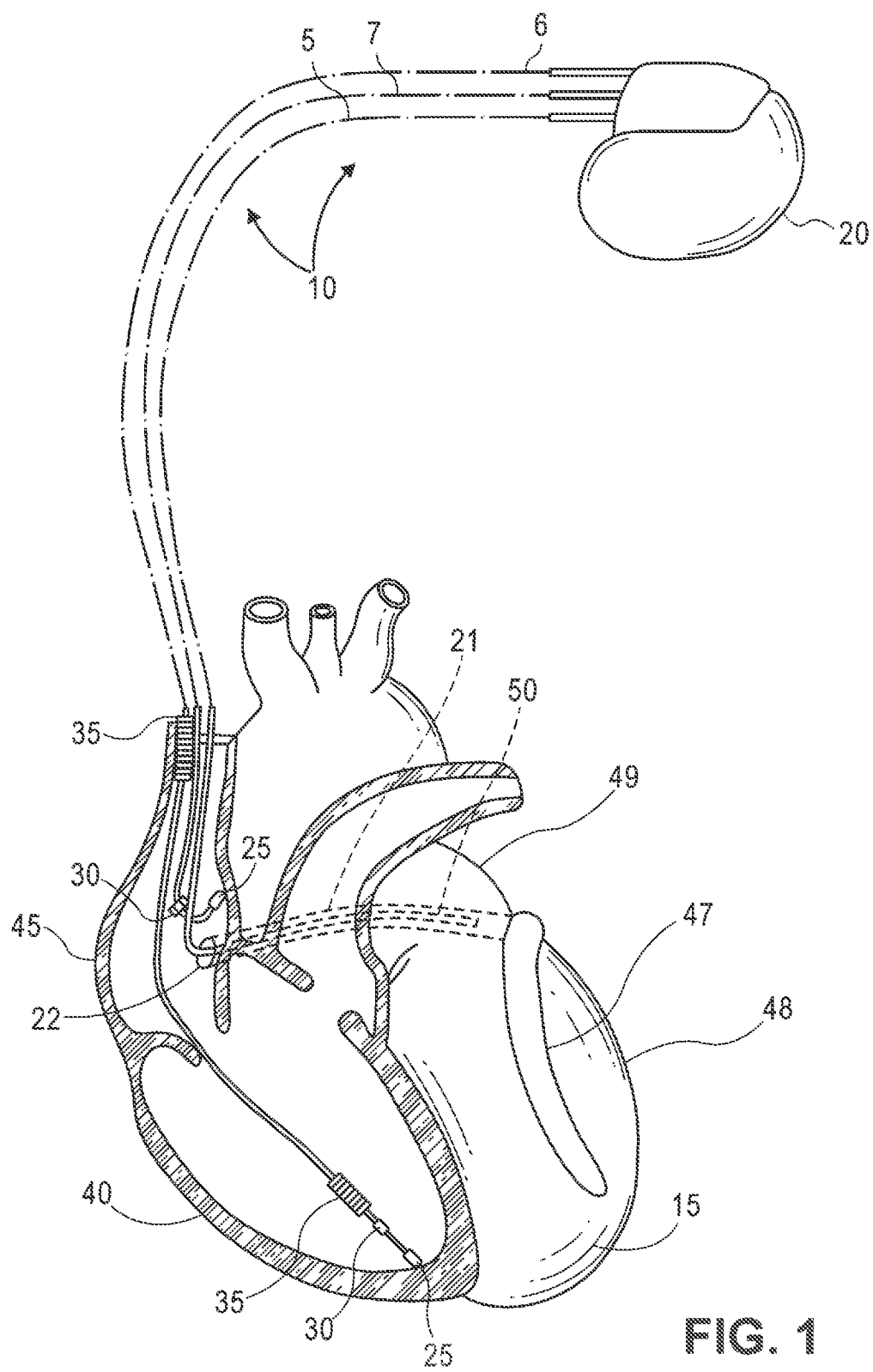
FIG. 1 is a diagrammatic depiction of an electrotherapy system electrically coupled to a patient heart as shown in an anterior view of the heart, a distal portion of a LV lead being implanted in the CS to facilitate CRT.

To begin the general, non-limiting discussion regarding CRT, reference is made to FIG. 1, which is a diagrammatic depiction of an electrotherapy system 10 electrically coupled to a patient heart 15 as shown in an anterior view. As shown in FIG. 1, the system 10 includes an implantable pulse generator (e.g., pacemaker, implantable cardioverter defibrillator ("ICD"), or etc.) 20 and one or more (e.g., three) implantable medical lead 5, 6, 7 electrically coupling the patient heart 15 to the pulse generator 10. While the following discussion will focus on the intraoperative optimization of the implantation of the left ventricular ("LV") lead 5 extending into the coronary sinus ("CS") 21 via the coronary sinus ostium ("OS") 22, it should be remembered that the system 10 may employ only the LV lead 5 or the LV lead 5 in conjunction with other leads, such as, for example, a right ventricular ("RV") lead 6 and/or right atrial ("RA") lead 7. The RV and RA leads 6, 7 may employ pacing electrodes 25, sensing electrodes 30 and shock coils 35 as known in the art to respectively provide electrical stimulation to the right ventricle 40 and right atrium 45 of the heart 15. Similarly, although not specifically depicted in FIG. 1, the LV lead 5 may also employ pacing electrodes, sensing electrodes and shock coils as known in the art to provide electrical stimulation to the left ventricle ("LV") 48 of the heart 15.

As can be understood from FIG. 1, which shows an anterior view of the patient heart 15, the CS 21 extends generally patient right to patient left from the OS 22 and, further, posterior to anterior until transitioning into the great cardiac vein 47, which then extends in a generally inferior direction along the anterior region of the left ventricle 48. In extending generally posterior to anterior from the OS 22 until transitioning into the great cardiac vein 47, the CS 22 is inferior to the left atrium ("LA") 49 and superior to the LV 48.

As indicated in FIG. 1, and as is often the case for CRT, the distal portion 50 of the LV lead 5 does not extend into the great cardiac vein 47, but is instead implanted in the CS 21 or vein branches extending off of the CS 21. However, the intraoperative CRT optimization systems and methods disclosed herein are readily applicable to LV lead placement in the CS 21, its vein branches extending therefrom, or even for LV lead placement in the great cardiac vein 47, if true CRT optimization is achieved by such LV lead placement.

Figure 2:
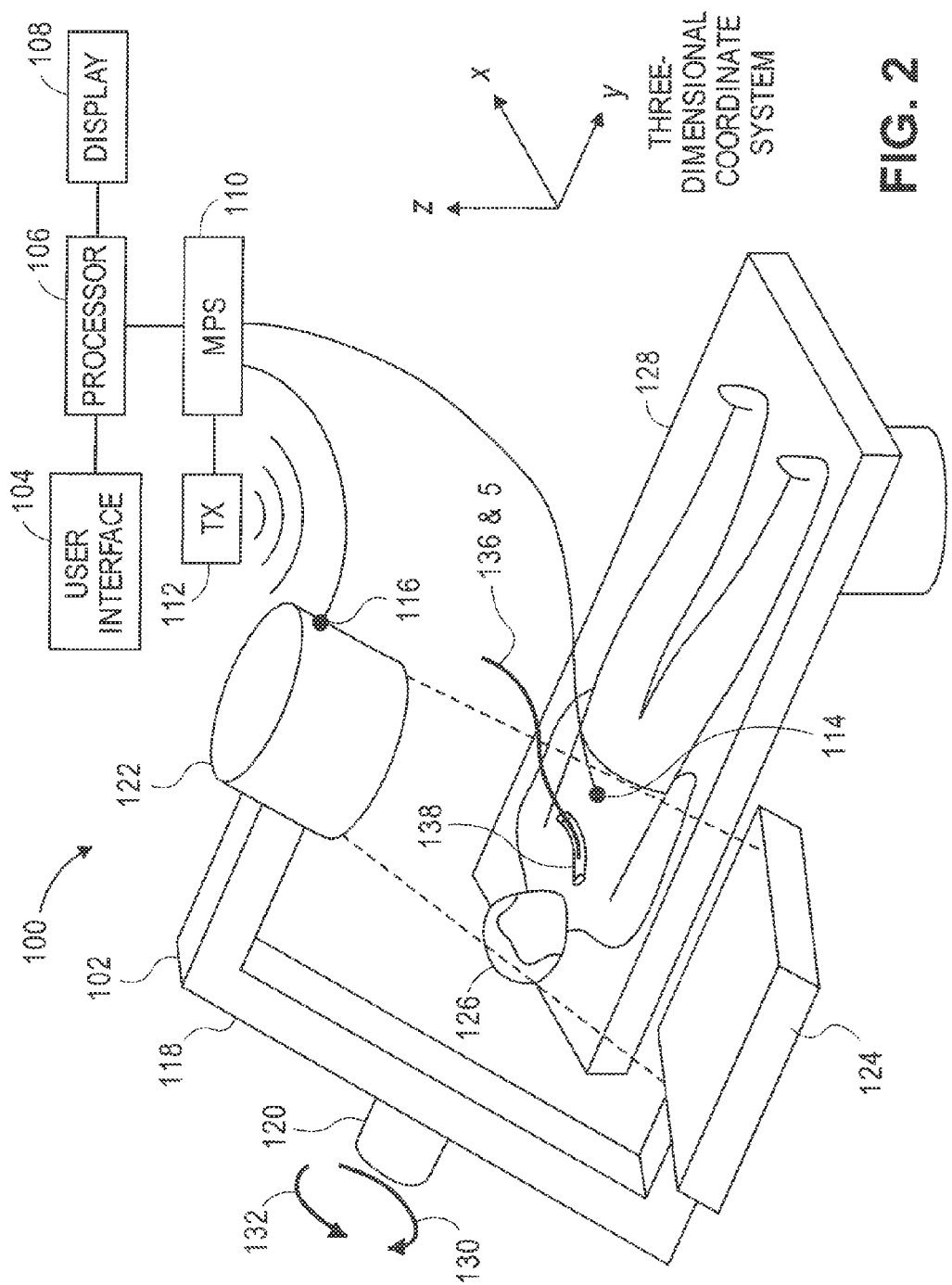
FIG. 2 is a schematic depiction of a navigation system and a system for intraoperative optimization of CRT.

FIG. 2 is a schematic depiction of an example navigation system 100 configured for intraoperative optimization of CRT. As shown in FIG. 2, the system 100 includes an image acquisition device 102, a user interface 104, a processor 106, a display 108, a medical positioning system (MPS) 110, a transmitter 112, and MPS sensors 114 and 116. The image acquisition device 102 includes a structural member 118, a moving mechanism 120, an emitter 122, and an image detector 124. The processor 106 is coupled with the user interface 104, display 108, and MPS 110. The MPS 110 is coupled with the transmitter 112 and MPS sensors 114 and 116. The moving mechanism 120, emitter 122, and image detector 124 are coupled with the structural member 118.

The MPS sensor 114 is firmly attached to the body of a patient 126 who is lying on a bed 128. The MPS sensor 116 is firmly attached to the image acquisition device 102. Each of the MPS sensors 114 and 116 responds to electromagnetic radiations which the transmitter 112 emits. The MPS 110 determines the position of the body of the patient 126, and the position of the image acquisition device 102, according to an output of the MPS sensors 114 and 116, respectively. Therefore, all movements of the image acquisition device 102 and of the body of the patient 126 are defined in a three-dimensional coordinate system respective of the MPS 110. In case the image acquisition device 102 is registered with the MPS 110, the MPS sensor 116 can be eliminated from the system 100. Instead of the MPS 110, other position detection systems can be employed to define the movements of the body of the patient 126 and of the image acquisition device 102, such as optical, acoustic, and the like.

The emitter 122 is located above the body of the patient 126. The image detector 124 is located below the body of the patient 126. The moving mechanism 120 enables the structural member 118 to rotate about an axis (not shown) substantially parallel with a longitudinal axis (not shown) of the bed 128, in directions referenced by arrows 130 and 132. The image acquisition device 102 may be a C-arm X-ray device. However, it is noted that the image acquisition device can be a computer tomography (CT) device, a magnetic resonance imager (MRI), positron emission tomography (PET), single photon emission computer tomography (SPECT), ultrasound image detector, infrared image detector, X-ray imager, optical coherent tomography detector (OCT), and the like. The user interface 104 can be tactile (e.g., keyboard, mouse, track-ball, touch-screen), acoustic (e.g., microphone, speaker), haptic (e.g., force-feedback joystick), and the like.

As can be understood from FIG. 2 a combination of a delivery tool 136 and a LV lead 5 are being navigated through a lumen 138 of the patient 126, the lumen being, for example, a subclavian vein and subsequent vascular lumens leading to the RA 45. As can be understood from FIG. 3, which is a left lateral posterior view of the patient heart 15, the CS 21 extending patient left and generally anterior from the OS 22 along the outer surface of the heart between the LV 48 and LA 49, the combination of the delivery tool 136 and the LV lead 5 of FIG. 2 have been navigated into the CS 21 from the RA 45 and the OS 22, as can be understood from FIG. 1.

FIGS. 4A and 4B are side view of distal regions of two different versions of the combination of the delivery tool 136 and the LV lead 5. As shown in FIG. 4A, the delivery tool 136 may be a guidewire, stylet or other delivery tool configuration adapted to extend through the interior of the LV lead 5. Oppositely and as illustrated in FIG. 4B, the delivery tool 136 may be a sheath, catheter, introducer other tubular delivery tool configuration adapted to extend about the LV lead 5. Regardless of the configuration of the delivery tool 136, the tool 136 will be configured to facilitate the tracking of the LV lead 5 through the vasculature and heart structure of the patient to deliver the distal end of the LV lead to a desired implantation site in the CS 21 or one of its branches. Also, regardless of the configuration of the delivery tool 136, the distal end of the tool 136 will have a MPS sensor 140 adapted to be three dimensionally tracked in a three dimensional coordinate system by the MPS 110 of the system 100 of FIG. 2.

As can be understood from FIGS. 2, 4A and 4B and by way of example, the MPS sensor 140 may be in the form of one or more coils, the three dimensional position of which can be sensed in a low-powered electromagnetic field generated by the transmitter 112, and the three dimensional position of the one or more coils being sensed by the MPS 110. Medical imaging taken by the image acquisition device 102 is provided to the processor 106, which generates two and/or three dimensional images of the patient vasculature and cardiac structures. The position of the MPS sensor 140 is overlaid on the two or three dimensional medical images and these overlaid images are displayed to the physician on the display 108, which allows the physician to visualize the tracking of the delivery tool 136 and the LV lead 5 supported thereon to the desired Implantation site in the OS 21 and its surrounding branches. In one embodiment, the system 100 employed herein is the MediGuide™ cardiovascular navigation system of St. Jude Medical, Inc., and the delivery tool 136 is a MediGuide Enabled™ device. Examples of MediGuide™ Technology may be found in U.S. Pat. No. 8,442,618, issued May 14, 2013, to Strommer et al.; U.S. Pat. No. 7,778,688, issued Aug. 17, 2010, to Strommer et al.; U.S. Pat. No. 7,386,339, issued Jun. 10, 2008, to Strommer et al.; U.S. Pat. No. 7,343,195, issued Mar. 11, 2008, to Strommer et al.; and U.S. Pat. No. 6,233,476, issued May 15, 2001, to Strommer et al., all of these patents being hereby incorporated by reference in their entireties.

While the present disclosure in discussed in the context of the MediGuide™ Technology of St. Jude Medical, Inc., and more specifically, coil sensors being tracked in a low-power medical field, in other embodiments, and as can be understood by those skilled in the art, the sensors could take the form of impedance based sensors and the low-powered magnetic field could be replaced by the magnetic module of the EnSite™ NavX™ Visualization and Navigation technology of St. Jude Medical, Inc.

Figure 3:
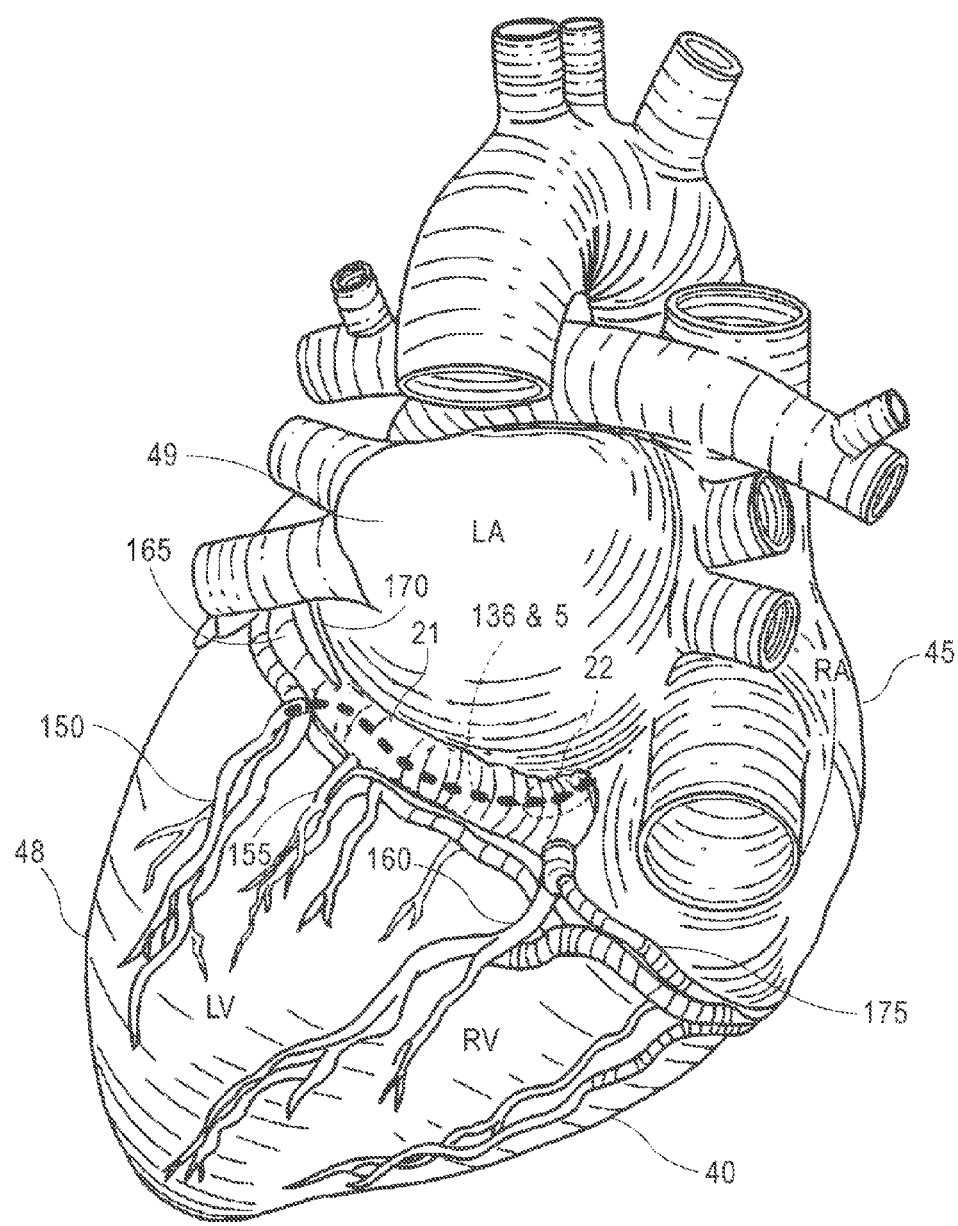
FIG. 3 is a left lateral posterior view of the patient heart, the CS extending patient left and generally anterior from the OS along the outer surface of the heart between the LV and LA, the system delivery tool of FIG. 2 and the LV lead of FIG. 1 having been tracked into the CS.

As can be understood from FIG. 3, the CS 21 has a number of immediately adjacent branch structures. For example, a left marginal cardiac vein ("LMV") 150, a posterior cardiac vein ("PCV") 155 and a middle cardiac vein ("MCV") 160 extend generally inferior off of the CS 21. A great cardiac vein ("GCV") 165 can be seen to extend generally anterior from the CS 21, and a vein of Marshall ("VM") 170 can be seen to extend generally anterior from the CS 21 and superior the GCV 165. A small cardiac vein ("SCV") 175 can be seen to extend patient right and generally posterior off of the CS 21. Depending on the individual, the mid-coronary sinus, which extends from the MCV 160 to the PCV 155, may have a diameter between approximately eight millimeters and approximately ten millimeters. Depending on the individual, the distal-coronary sinus, which extends from the PCV 155 to the GCV 165, may have a diameter between approximately five millimeters and approximately seven millimeters. Depending on the patient needs and the proscribed CRT, any one or more of these CS related vascular structures may provide an optimal location for implantation of a LV lead. For example, as depicted in FIG. 3, the combination of the delivery tool 136 and the LV lead 5 are shown to have their combined distal ends beginning to enter the LMV 150 from the CS 21. The delivery tool 136 and LV lead 5 could be similarly positioned to enter into any of the other above-listed branches off of the CS 21 for implantation of the LV lead distal end at such branch locations.

Once the delivery tool 136 has been used to implant the LV lead 5 at a candidate implantation site, the delivery tool 136 can then be withdrawn from the LV lead and re-tracked into the CS 21 for placement at a first measurement site to begin the CRT optimization methodology as described below.

Alternatively, instead of employing a single delivery tool, which is sensor equipped, to both deliver the LV lead and also sense displacement at a first and subsequent measurement locations as discussed below, two delivery tools may be employed, wherein one delivery tool is non-sensor equipped and the other delivery tool is sensor equipped. The non-sensor equipped delivery tool can be used to implant the LV lead at the candidate implantation site and the sensor-equipped delivery tool can simply be tracked to the first measurement site to begin with in preparation for sensing displacement at the first and subsequent measurement locations.

b. CRT Optimization Methodology

As mentioned above, analysis in real time of a path of a displacement of a navigation or medical positioning system (MPS) sensor 140 supported on a lead delivery tool 136, or even the LV lead itself, can be used to optimize LV lead implant location and pulse generator programming settings. The sensor motion path recorded at each measurement site includes parameters or features calculated or derived from the motion of the MPS sensor 140 during a complete cardiac cycle, and these parameters or features of the sensor motion path can be used to determine the efficiency of the heart motion at a certain implant location and under different pacing settings.

Figure 5:
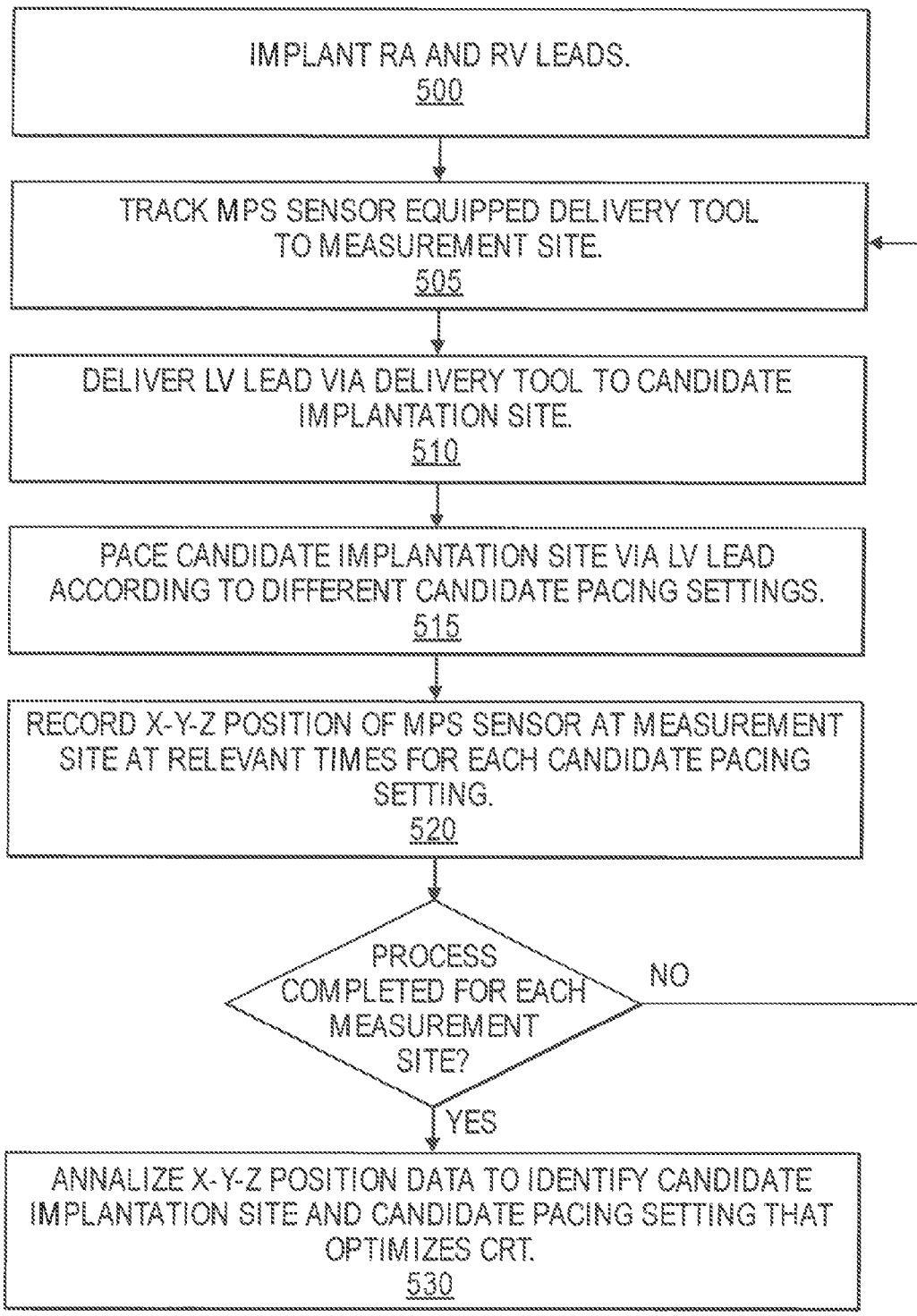
FIG. 5 is a flow chart outlining the CRT optimization methodology.
Figure 6A:
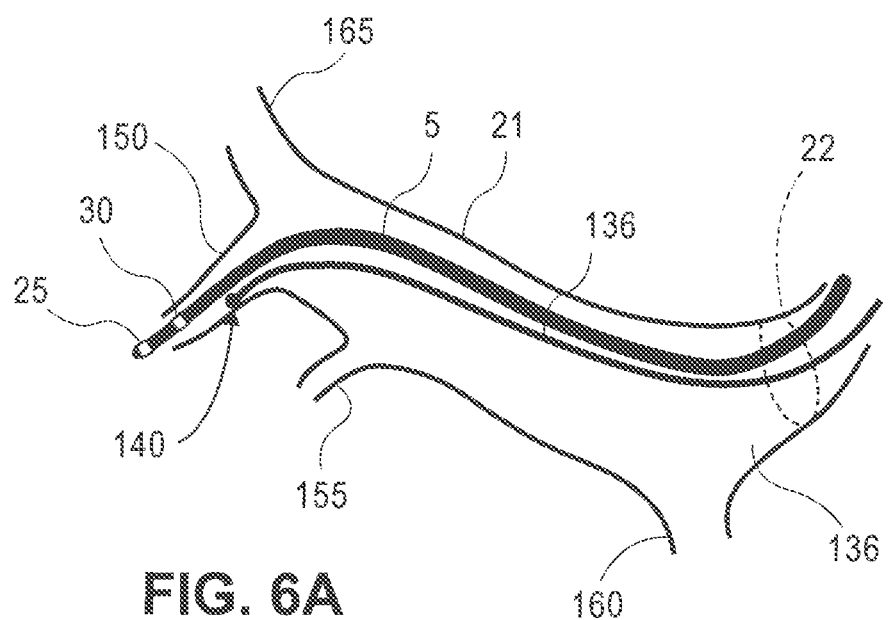
FIG. 6A-6D are diagrammatic depictions of the CS and its branches indicating the MPS sensor at successive measurement locations and the distal end of the LV lead positioned at a candidate implant location and administering candidate pacing sequences in the course of implementing the optimization methodology disclosed herein.
Figure 6B:
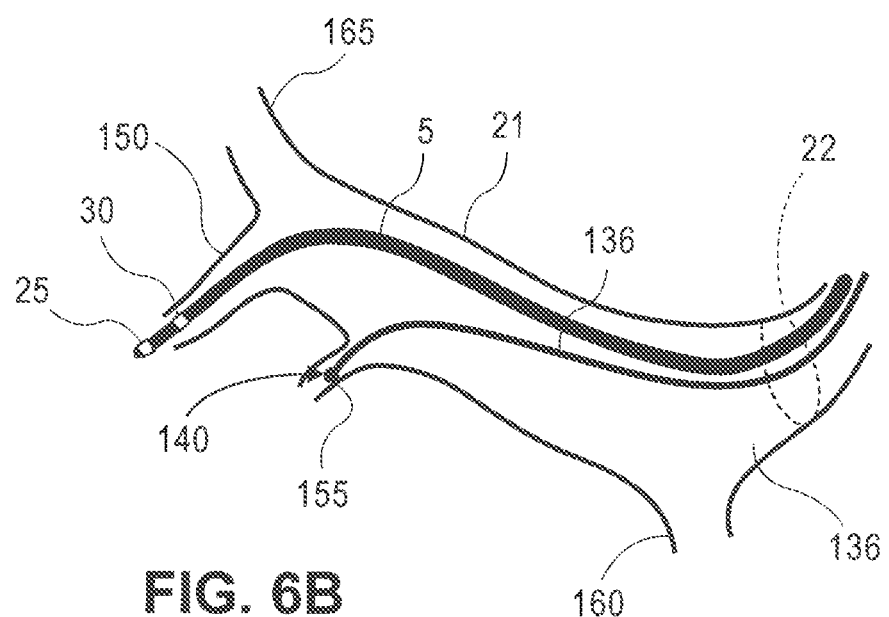
Figure 6C:
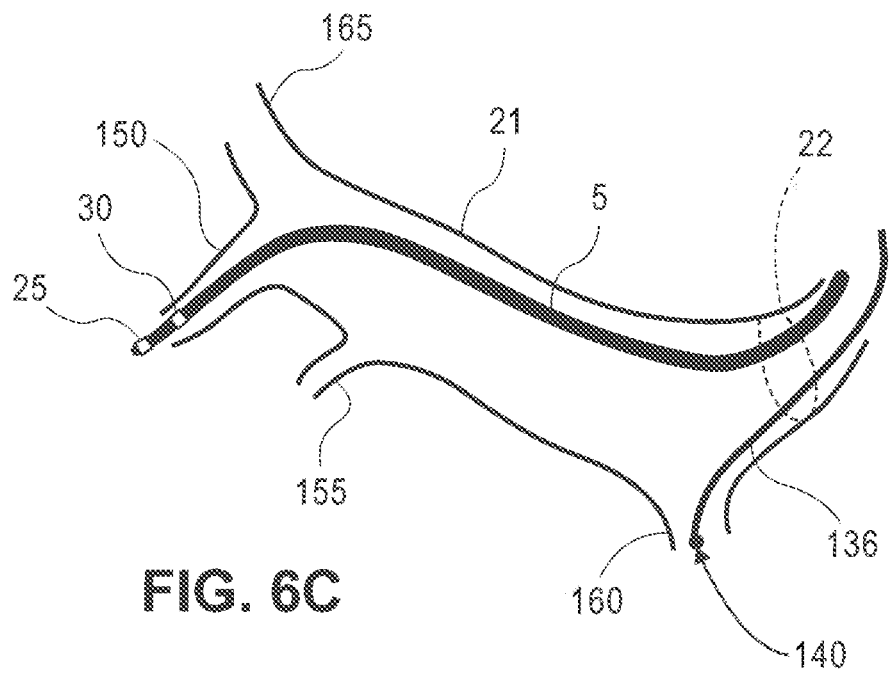
Figure 6D:
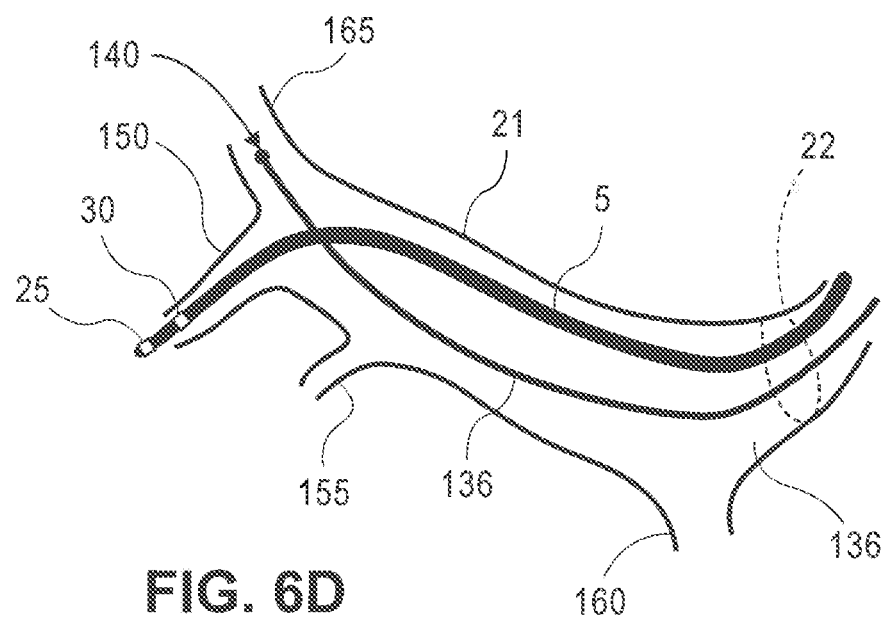

As will be understood from the immediately following discussion with respect to FIG. 5, the measurement process can be repeated at second, third, fourth, and yet additional measurement locations (e.g., at or in the CS 21 or one of its associated branches 150, 155, 160, 165, 170, 175 as depicted in FIG. 3). As will be discussed with respect to FIG. 7 below, once the sensor motion path data has been obtained via the methodology outlined with respect to FIG. 5, the sensor motion path data can be assessed for parameters or features such as, for example, total circumference trajectory, longest motion vector, eccentricity and hysteresis to identify both the optimal CRT implant location and the optimal programming setting for the pulse generator 20.

1. Obtaining Sensor Motion Path Data at Each Measurement Site

FIG. 5 is a flow chart outlining a method of optimizing CRT and, more specifically, a method of obtaining sensor motion path data at each measurement site that can then be analyzed to determine an optimized CRT. FIGS. 6A-6D are diagrammatic depictions of the CS 21 and the beginnings of its associated branches 150, 155, 160, 165, wherein the MPS sensor 140 of the delivery tool 136 is shown at successive measurement locations and the distal region of an LV lead 5 is depicted as being located at a candidate implant location. The CRT optimization method will now be discussed with respect to FIGS. 5 and 6A-6D.

The RA lead 7 and RV lead 6 are first implanted, as can be understood from FIG. 1 [block 500]. An MPS sensor equipped delivery tool 136 is tracked to a first measurement site, such as, for example, the LMV 150 as can be understood from FIG. 6A [block 505]. The delivery tool 136 may be a guidewire, stylet, catheter, sheath, introducer, etc., as discussed above with respect to FIGS. 4A and 4B. The LV lead 5 is delivered to the LMV 150, which, in this example, is the candidate implantation site, as can be understood from FIG. 6A [block 510]. The delivery of the LV lead 5 to the LMV 150 may take place with the MPS sensor equipped delivery tool 136 or via another delivery tool. Via its electrodes 25, 30, the LV lead 5 administers pacing to the candidate implantation site according to different candidate pacing settings [block 515]. For the first measurement site in the LMV 150, the MPS system 110 records the x-y-z three dimensional position of the MPS sensor 140 in the three dimensional x-y-z coordinate system at relevant times of each candidate pacing setting [block 520]. Such recording of the x-y-z position of the MPS sensor 140 over the course of a cardiac cycle for a candidate pacing setting defines a motion path of the MPS sensor 140 at the first measurement site in the LMV 150. This process of pacing with candidate pacing settings at the candidate implantation site in the LMV 150 is repeated for each time MPS sensor equipped delivery tool 136 is positioned at a new measurement site, as can be understood from FIGS. 6B-6D and FIG. 5. Once the process has been completed for each measurement site 150, 155, 160, 165 as illustrated in FIGS. 6A-6D or even other measurement sites, such as, for example, 170 and 175 as can be understood from FIG. 3, the x-y-z position data, and more specifically, the features of the defined motion path of the MPS sensor, can be analyzed as discussed below in detail with respect to FIGS. 7-17 to identify the candidate implantation site(s) and candidate pacing setting(s) that optimizes CRT [block 530]. Specifically, the x-y-z position data can be used to determine the features of the MPS sensor motion path, namely, the total circumference of trajectory, longest motion vector, eccentricity and hysteresis, associated with each measurement site for the candidate implantation site and its candidate pacing settings to determine which combination of candidate implantation site and candidate pacing setting best optimizes the CRT.

Depending on time constraints, the needs of the patient, and the desires of the physician, the process of FIG. 5 can be repeated for other candidate implantation sites. For example, once the first candidate implantation site in the LMV 150 is assessed as explained above with respect to FIGS. 5 and 6A-6D, the LV lead 5 could be positioned in one of the other CS branches, for example, the PCV 155, which can then serve as a second candidate implantation site where candidate pacing settings are administered as the displacement of the MPS sensor 140 is tracked during such pacing administrations when the MPS sensor 140 is positioned in turn at each measurement site 150, 155, 160, 165, etc., similar to as discussed above with respect to FIGS. 5 and 6A-6D. The process could even be repeated to the extent that the process is completed for each candidate implantation site.

It should be noted that while the above-described methodology employs an MPS sensor 140 mounted on a delivery tool 136, in some embodiments, the MPS sensor 140 could simply be part of the distal region of the LV lead 5.

Ultimately, the selected candidate implantation site(s) and candidate pacing setting(s) will be those that provide the most optimized MPS sensor motion path, specifically, the most optimized the total circumference of trajectory, longest motion vector, eccentricity and hysteresis. Tracking the MPS sensor motion path at a measurement location during administration of a candidate pacing setting at a candidate implantation site acts as a surrogate of the heart tissue motion at the measurement location during the candidate pacing setting. Tracking the MPS sensor motion path at successive measurement locations under the same implant and pacing constraints allows the determination of which candidate implantation site and candidate pacing setting provides the most efficient and desirable heart tissue motion for CRT.

In other words, the motion path of MPS sensors 140 within the CS 21 and each LV branch 150, 155, 160, 165, 170, 175 represents a correlation to ventricular wall motion. During cardiac contraction and relaxation, the longer the longest motion vector and the more optimized the total circumference of trajectory, eccentricity and hysteresis of the motion path, the better the heart movement. Thus, the better the heart moves in relation to a specific candidate pacing setting at a specific candidate implantation site, the more likely these are the pacing setting and implantation site that will provide the optimized CRT for the patient.

2. Analyzing Sensor Motion Path Data

As discussed above with respect to FIG. 5, once the sensor motion path data is obtained for a measurement location, the data can be analyzed [block 530]. As can be understood from FIG. 7, analysis of the sensor motion path data may begin with normalizing the data [block 700]. For example, a control for the data may be employed with the raw x-y-z MPS sensor position data. In other words, the raw x-y-z MPS sensor position data may need to be normalized or otherwise adjusted before being assessed for motion path features (e.g., total circumference of trajectory, longest motion vector, eccentricity and hysteresis) as described below.

For example, AAI mode may be used as a reference control for CRT optimization, and the change between DDD with different atrioventricular delays ("AVD") and VVI with respect to AAI may be used as criteria for optimization. DDD-RV pacing at a nominal AVD, or VVI-RV only may also be used as a reference configuration, particularly in patients with AV block or permanent AF.

For each type of candidate pacing setting, the recorded MPS sensor x-y-z positional data is then parsed into individual beats based on the ECG. The MPS sensor motion path features (e.g., total circumference of trajectory, longest motion vector, eccentricity and hysteresis) for each type of candidate pacing setting is calculated. The changes or the normalized changes of the motion path features are also derived, and, as already noted above, the lead location and pacing settings are optimized based on the changes of the features of the MPS sensor motion path.

Figure 8A:
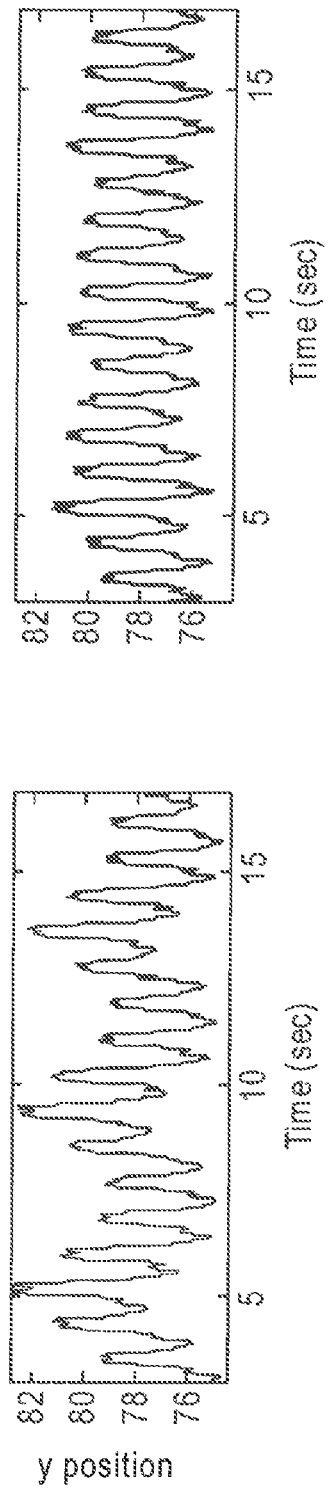
FIG. 8A are representative graphical plots of the MPS sensor x-y-z position data in the y-direction during 20 second continuous heart beats (see the left plot panel of FIG. 7) and after respiration and movement compensation (see the right plot panel of FIG. 7).
Figure 8B:
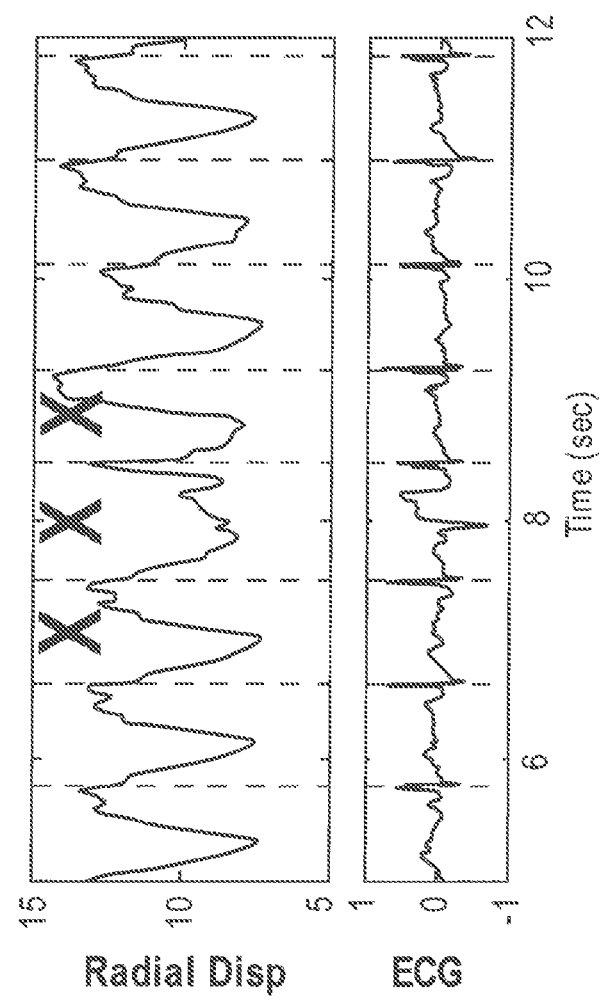
FIG. 8B is a graphical plot indicating that the ectopic beats are excluded from the y-direction data of FIG. 7 to ensure data quality.

FIG. 8A includes representative graphical plots of the navigation or medical positioning system (MPS) sensor path x-y-z position data in the y-direction during 20 second continuous heart beats (see the left plot panel of FIG. 8A) and after respiration and movement compensation (see the right plot panel of FIG. 8A). As can be understood from each "X" in FIG. 8B, the ectopic beats may be excluded from the y-direction data of FIG. 8A to ensure data quality. In one embodiment, the MPS sensor motion paths for the selected beats are ensemble-averaged to get a representative motion profile over the cardiac cycle, after which the MPS sensor motion path features (e.g., total circumference of trajectory, longest motion vector, eccentricity and hysteresis) at each location can be calculated.

As an alternative to ensemble-averaging the motion paths, the various motion path characteristics such as, e.g., total circumference of trajectory, longest motion vector, eccentricity and hysteresis, may be computed on a single-beat basis, and the individual measures averaged over three to 10 beats of the same rhythm. This approach can account for both beat-to-beat variability and also for relevant respiratory-modulated changes associated with, for example, differing intra-thoracic and filling pressures.

To optimize CRT during the lead implant, the physician places a MPS sensor enabled delivery tool and LV lead (or, alternatively, a MPS sensor enabled LV lead) into a CS 21 or a branch thereof, such as posterolateral vein. The x-y-z position coordinate data of the MPS sensor 140 are measured as successive measurement locations for each candidate implantation location with different candidate pacing interventions such as, e.g., AAI, VVI, DDD, each with applicable different AV delays. Among these candidate pacing interventions, AAI is considered as baseline, for example, to normalize the x-y-z position coordinate data. The x-y-z position coordinates of the MPS sensor 140 are tracked to define a MPS sensor motion path 200 for each candidate pacing intervention at each measurement location.

The change of the MPS sensor motion path features (e.g., total circumference of trajectory, longest motion vector, eccentricity and hysteresis) between each candidate pacing setting and the baseline pacing setting (e.g., AAI) are estimated. The candidate implantation location and corresponding candidate pacing setting resulting in the maximum change of MPS sensor motion path feature(s) is deemed as the optimal lead location and device settings. The change of MPS sensor motion path feature(s) is defined as: change of MPS sensor motion path feature=$(P_I-P_{AAI})$, wherein $P_I$ is the change in the MPS sensor motion path feature for a candidate pacing setting, and $P_{AAI}$ is the MPS sensor motion path feature for the control.

The change in the MPS sensor motion path feature for a candidate pacing setting can be normalized and then used to optimize the CRT implant. The normalized change in the MPS sensor motion path feature is defined as: normalized change in the MPS sensor motion path feature=$(P_I-P_{AAI})/P_{AAI}$, wherein $P_I$ is the change in the MPS sensor motion path feature for a candidate pacing setting, and $P_{AAI}$ is the MPS sensor motion path feature for the control.

Figure 7:
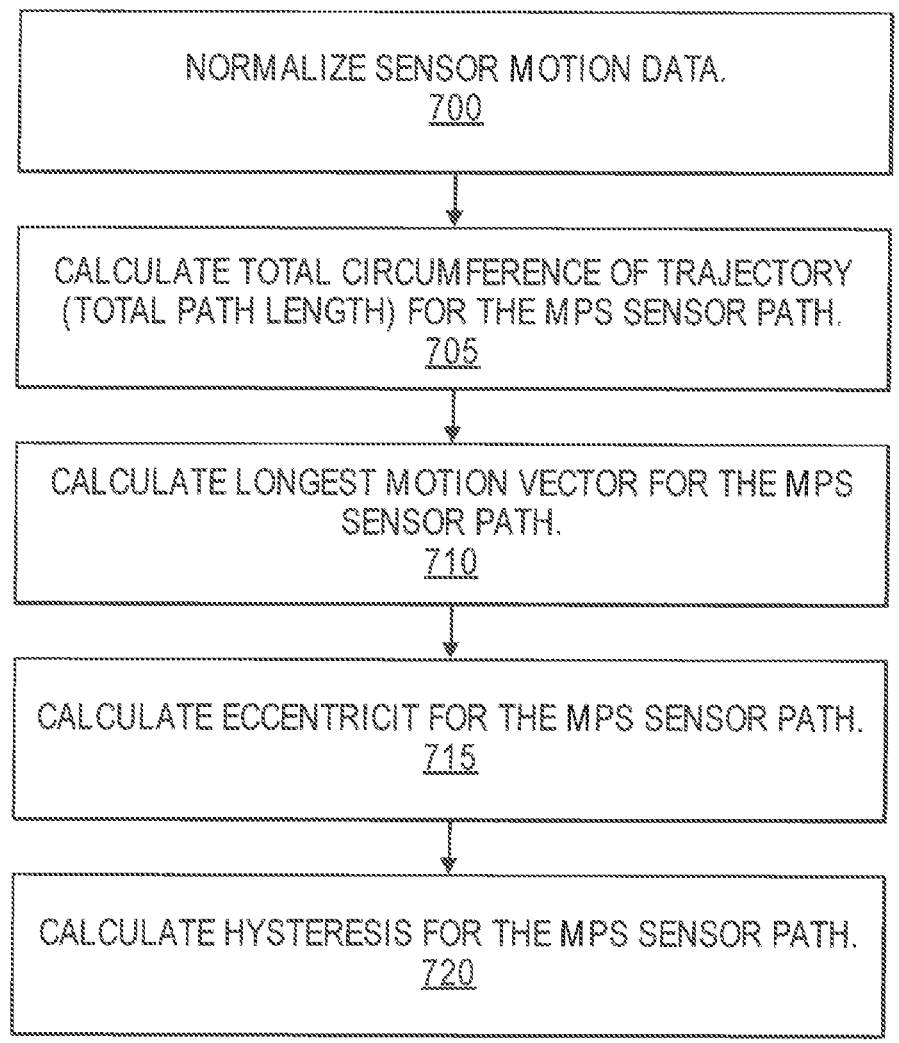
FIG. 7 is a flow chart outlining analyzing sensor motion path data obtained via the process outlined in FIG. 5.
Figure 9A:
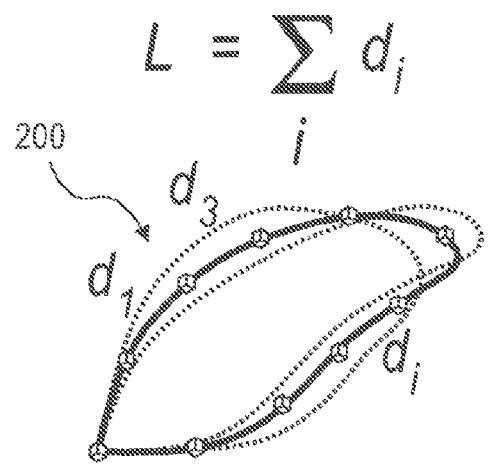
FIG. 9A illustrates MPS sensor motion paths and a corresponding equation for determining total MPS sensor motion path length.

As indicated in FIG. 7, once the sensor motion data has been normalized, the sensor motion data can then be analyzed at each measurement site with respect to total circumference of trajectory or total path length for the MPS sensor path [block 705]. For example, FIG. 9A illustrates MPS sensor motion paths and a corresponding equation for determining total length "L" of the MPS sensor motion path or, in other words, the total circumference of trajectory. As can be understood from FIG. 9A, the total length L of the MPS sensor motion path 200 with sample location points $d_1$, $d_2$ and $d_3$ can be determined as the sum of sensed location points $d_1$, $d_2$, $d_3$, and $d_t$ over a complete cardiac cycle. The sensor motion path 200 is the result of three dimensional measurements and may be a three dimensional looped path. Also, multiple sensor motion paths may be taken over the course of multiple complete cardiac cycles, resulting in multiple paths 200 being recorded as indicated in FIG. 9A. These multiple paths 200 may be averaged or normalized.

Typically, the greater the total length L of the motion path 200, the better optimized the heart tissue displacement. However, besides the total circumference of trajectory or total length L of the MPS sensor motion path 200, the shape of the path 200 can also be analyzed for other features of the motion path 200, including the longest motion vector, eccentricity and hysteresis of the MPS sensor motion path 200 to further identify the best optimization of the CRT. Specifically, in one embodiment, all four of these features can be used to determine the heart wall motion and, more specifically, analyzed to identify the most efficient pacing location and pacing sequence.

Figure 9B:
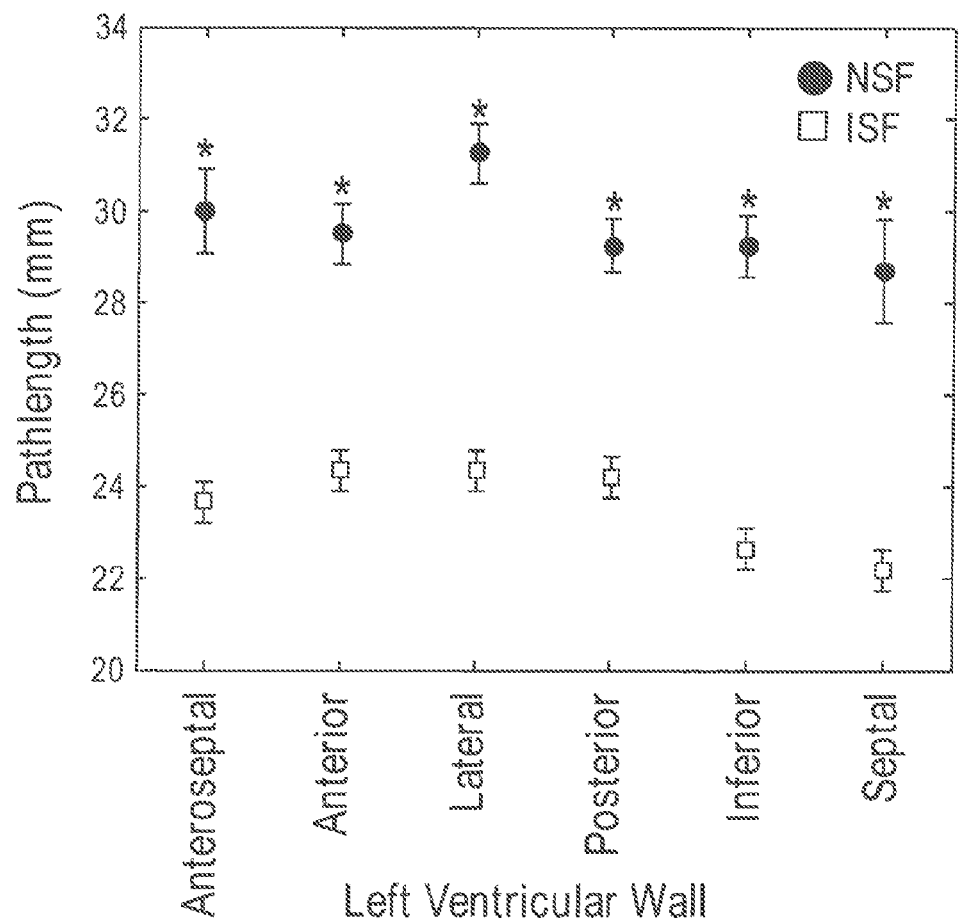
FIG. 9B is a graphical depiction of system test results illustrating total path length within a MPS sensor motion path associated with candidate MPS sensor locations on an endocardial surface averaged within each of six LV wall segments (i.e., anteroseptal, anterior, lateral, posterior, inferior, and septal).

FIG. 9B is a graphical depiction of system test results illustrating total path length within a MPS sensor motion path associated with candidate MPS sensor locations on an endocardial surface averaged within each of six LV wall segments (i.e., anteroseptal, anterior, lateral, posterior, inferior, and septal). As can be understood from FIG. 9B, the test results show that patients with normal systolic function (NSF) have significantly (as indicated by asterisks, $p<0.05$) more LV motion (e.g., more path length L as discussed with respect to FIG. 9A) in all six LV walls than patients with impaired systolic function (ISF). The test results also show that the normal LV systolic function patients show the most movement in the lateral free wall and the least motion in the septal wall, which is what would be expected. These test results indicate that MPS sensors 140, when employed as described above, can accurately determine the wall motion of the heart using MPS sensor motion path concepts described herein.

Figure 10:
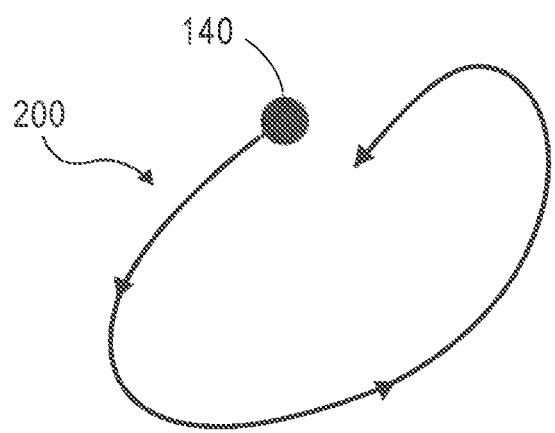
FIG. 10 is a schematic depiction of a motion path of a MPS sensor for a candidate pacing setting at a candidate implantation site.

Besides an assessment of the motion path 200 associated with the MPS sensor x-y-z position data according to path length L, the assessment of the motion path also includes the longest motion vector, eccentricity and hysteresis of the MPS sensor motion path 200. FIG. 10 illustrates a motion path 200 of a MPS sensor 140 for a candidate pacing setting at a candidate implantation site, the motion path 200 being similar to that discussed with respect to FIG. 9A. This motion path 200 has been normalized and parsed as described above.

Figure 11:
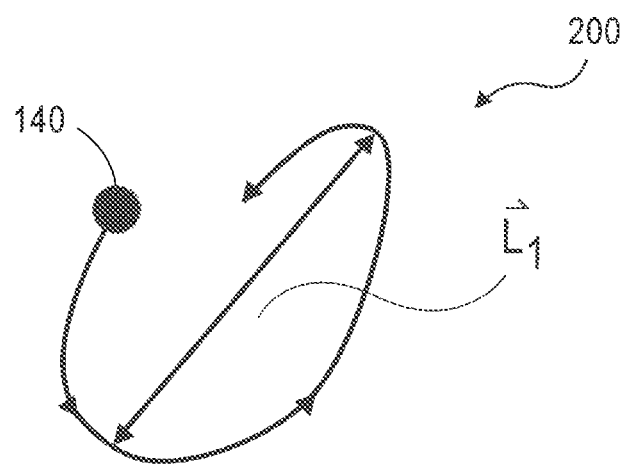
FIG. 11 is the same as FIG. 10, except illustrating the measurement of the longest vector length (i.e., the longest motion vector) spanning the total circumference of trajectory of the motion path of the MPS sensor.

As indicated in FIG. 7, the sensor motion data can be analyzed at each measurement site with respect to longest motion vector for the MPS sensor path [block 710]. FIG. 11 indicates the calculation of the length of the longest motion vector $L_1$, which is the longest motion vector spanning the MPS sensor motion path 200 of FIG. 10. Typically, the longer the length of the longest motion vector $L_1$, the better optimized the heart tissue displacement. However, further assessment of the motion path 200 according to eccentricity and hysteresis can more definitively assess the motion path 200 with respect to optimization.

Figure 12:
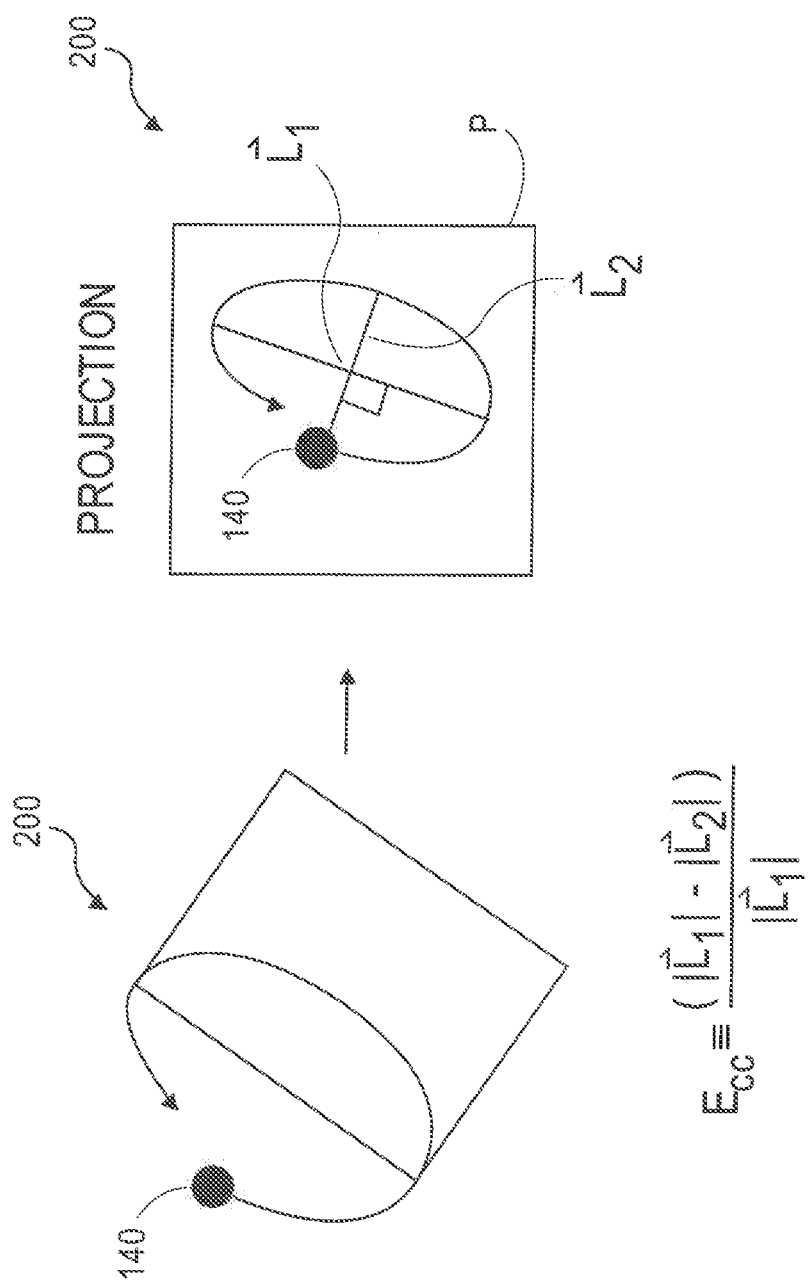
FIG. 12 is a schematic depiction of the determination of a shortest vector length and employing the longest vector length and the shortest vector length in a determination of the eccentricity of the total circumference of trajectory of the motion path of the MPS sensor.

As indicated in FIG. 7, the sensor motion data can be analyzed at each measurement site with respect to eccentricity for the MPS sensor path [block 715]. FIG. 12 illustrates a process for calculating the eccentricity associated with the MPS sensor motion path 200 of FIG. 10. As can be understood from FIG. 12, a second vector length $L_2$ is found relative to the motion path 200. The second vector length $L_2$ is calculated as the shortest vector length $L_2$ that extends across the motion path 200 while intersecting the longest vector length $L_1$ at is midpoint and in a perpendicular manner while fitting in a plane P that also includes both the longest vector length $L_1$ and the motion path 200, the MPS sensor motion path 200 being the normalized motion path taken by the MPS sensor 140 during a full cardiac cycle at a specific candidate implantation site undergoing a specific candidate pacing setting.

Figure 13:
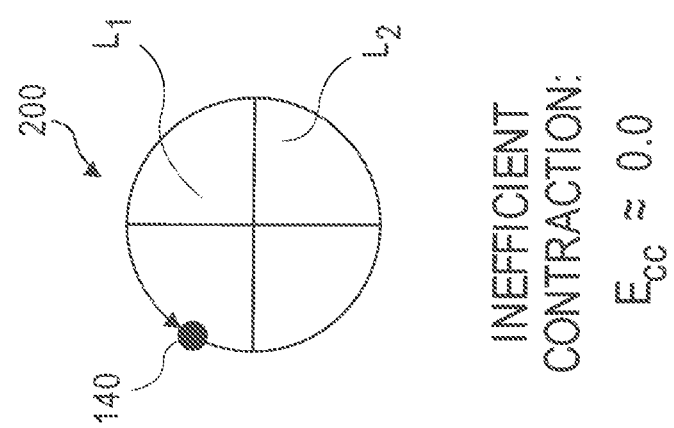
FIG. 13 illustrates a total circumference of trajectory with eccentricity of zero, which is representative of inefficient contraction of the cardiac tissue at the candidate implantation site under the candidate pacing setting associated with the path motion of the MPS sensor.
Figure 14:
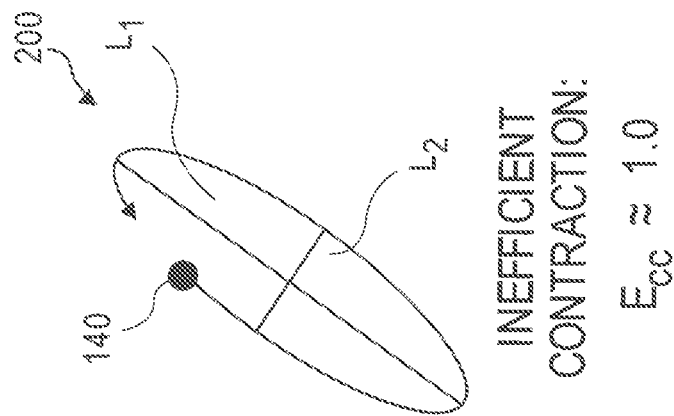
FIG. 14 illustrates a total circumference of trajectory with eccentricity of nearly one, which is representative of efficient contraction of the cardiac tissue at the candidate implantation site under the candidate pacing setting associated with the path motion of the MPS sensor.

As indicated in FIG. 12, eccentricity is defined as the ratio $Ecc=(L_1-L_2)/L_1$, and will range between $Ecc=0$ for a perfectly circular MPS sensor motion path (as shown in FIG. 13) and $Ecc=1$ for an infinitely skinny linear back-and-forth MPS sensor motion path (as can be understood from FIG. 14). Eccentricity closer to one is preferred, indicating an efficient contraction and relaxation of the cardiac tissue of the candidate implantation site under the candidate pacing setting. The closer the eccentricity is to zero, the greater the inefficiency of the contraction and relaxation of the cardiac tissue of the candidate implantation site under the candidate pacing setting. Accordingly, optimized CRT will have a MPS sensor motion path 200, which is representative of the cardiac cycle motion path of the associated cardiac tissue of the candidate implantation site during a candidate pacing setting, that has an eccentricity that is as close to one as possible.

As indicated in FIG. 7, yet another assessment of the motion path 200 of the MPS sensor x-y-z position data includes the hysteresis of the MPS sensor motion path 200 [block 720]. The hysteresis, like the eccentricity, can be used to characterize the efficiency of the contraction-relaxation motion path of the cardiac tissue at the candidate implantation site and during the candidate pacing setting. The process of calculating the hysteresis of the motion path 200 begins the same as already discussed above in reference to FIGS. 10 and 11 with respect to the calculation of the eccentricity. Specifically, again referencing FIGS. 10 and 11, the hysteresis assessment begins by computing the longest vector length $L_1$ spanning the motion path 200. This longest vector length $L_1$ is the longest motion vector, which is a feature of the MPS sensor motion path 200.

Unlike "classic" hysteresis, which is defined simply as the area enclosed in a stress-strain or force-length loop of loading and unloading, the hysteresis calculation disclosed herein employs two parameters. These two parameters are a first hysteresis parameter $H_1$ and a second a first hysteresis parameter $H_2$, and their calculations are graphically depicted in FIG. 15.

Figure 15:
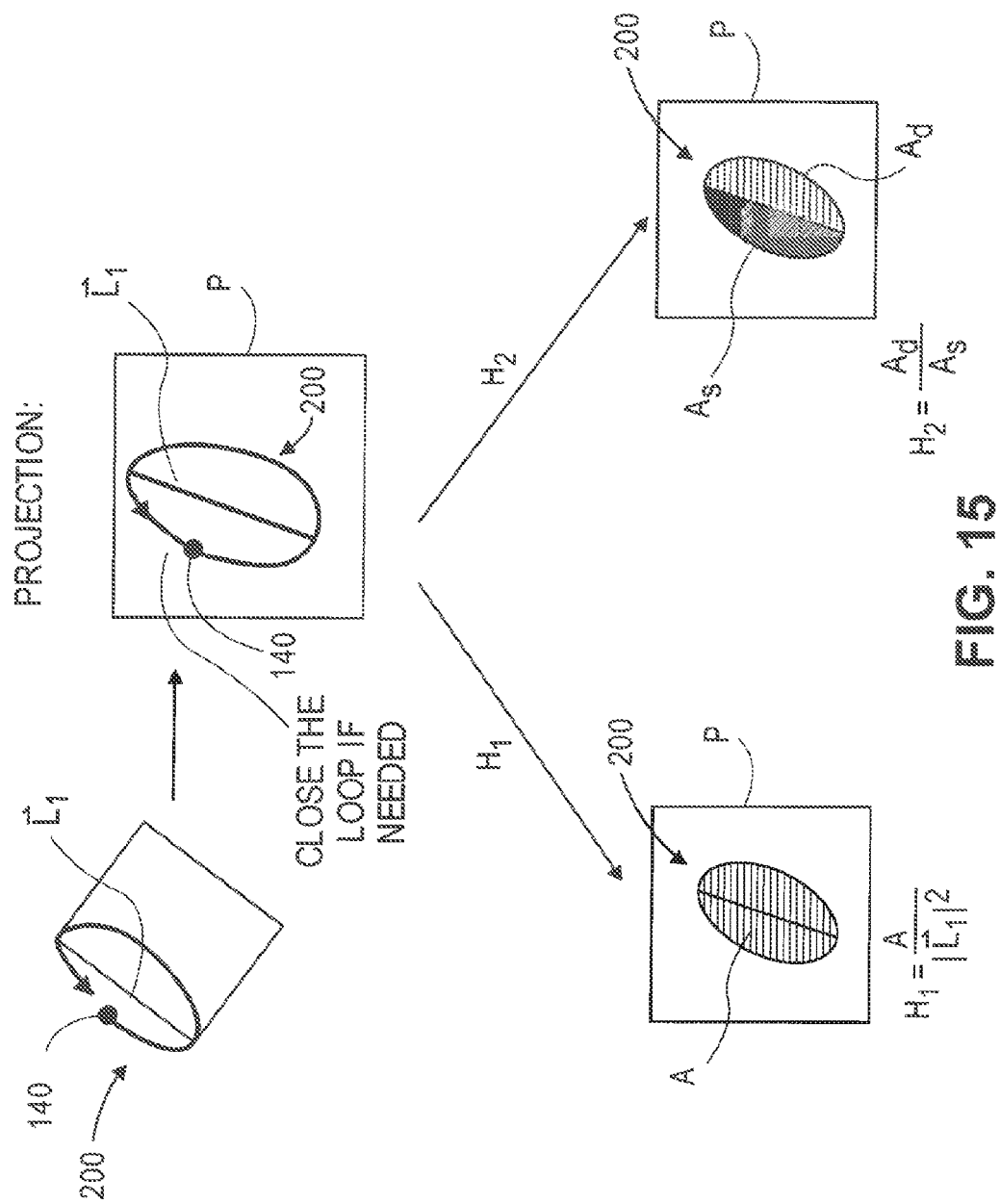
FIG. 15 is a diagrammatic depiction of methods of calculating two hysteresis patterns from the MPS sensor motion path.

As can be understood from the upper portion of FIG. 15, the MPS sensor motion path 200 may need to be closed to form a closed loop if it is not already. Preferably, although not necessary, the MPS sensor motion path 200 and the longest length vector $L_1$ are then projected onto a plane P that contains both these elements. Since the MPS sensor motion path 200 is likely to be a three dimensional motion path 200, the motion path 200 and the longest length vector $L_1$ may be fit onto the plane P via a best fit constraint.

As can be understood from the lower right of FIG. 15, the first hysteresis parameter $H_1$, can be calculated by taking the area A of the of the total circumference of trajectory of the MPS sensor motion path 200 and dividing by the longest length vector $L_1$ squared to normalize the overall loop size (i.e., $H_1=A/L_1^2$). Thus, the first hysteresis parameter $H_1$ is a dimensionless parameter where the closer the value is relative to $\pi/2$, the less efficient the contraction (i.e., more roundabout motion, and less in-and-out motion), as can be understood from FIG. 16. Conversely, the smaller the first hysteresis parameter $H_1$ is relative to $\pi/2$, the more efficient the contraction (i.e., less roundabout motion, and the more in-and-out motion), as can be understood from FIG. 17.

The second hysteresis parameter $H_2$ is similarly defined as the first hysteresis parameter $H_1$, but also accounts for systolic versus diastolic motion. For example, as can be understood from the lower left of FIG. 15, the calculation of the second hysteresis parameter $H_2$ begins by taking the area A of the of the total circumference of trajectory of the MPS sensor motion path 200 and splitting it by the longest length vector $L_1$ to obtain the systolic area $A_s$, which is the portion of the area A that is between the longest length vector $L_1$ and the portion of the motion path 200 associated with systolic contraction. The calculation continues by also determining the diastolic area $A_d$, which is the portion of the area A that is between the longest length vector $L_1$ and the portion of the motion path 200 associated with the diastolic motion (relaxation). The calculation of the second hysteresis parameter $H_2$ concludes by dividing the diastolic area $A_d$ by the systolic area $A_s$ (i.e., $H2=A_d/A_s$).

Figure 16:
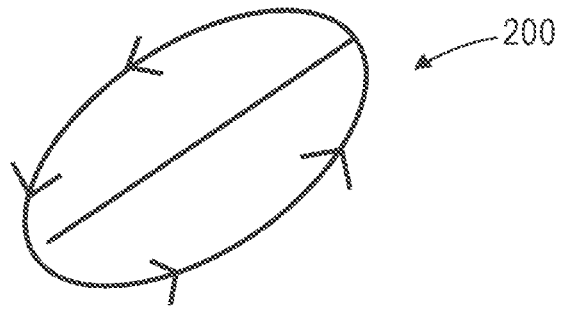
FIG. 16 is a diagrammatic depiction of an MPS sensor motion path associated with an inefficient cardiac tissue contraction.
Figure 17:
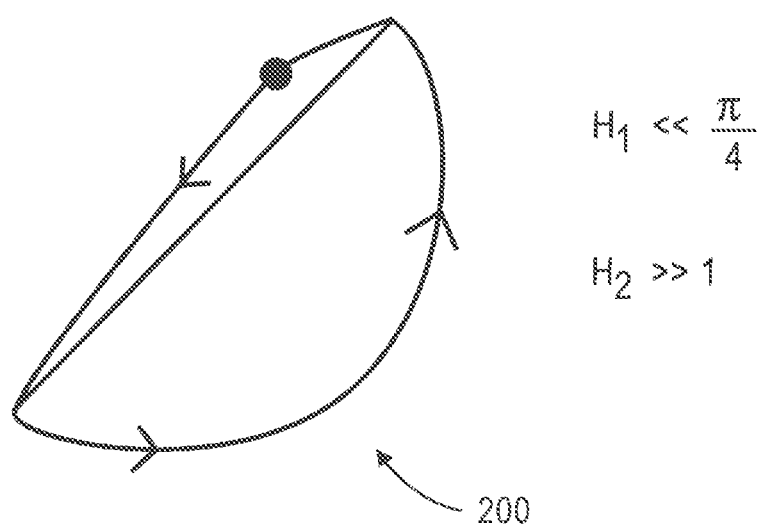
FIG. 17 is a diagrammatic depiction of an MPS sensor motion path associated with an efficient cardiac tissue contraction.

Thus, the second hysteresis parameter $H_2$ is a dimensionless parameter where the closer the value is relative to one, the less efficient the contraction (i.e., more roundabout motion, and the less in-and-out motion), as can be understood from FIG. 16. Conversely, the larger the second hysteresis parameter $H_2$ is relative to one, the more efficient the contraction (i.e., less roundabout motion, and the more in-and-out motion), as can be understood from FIG. 17. The increasing efficiency as the second hysteresis parameter $H_2$ is increasingly greater than one pertains to small systolic area $A_s$ relative to larger diastolic area $A_d$.

In summary, the CRT optimization methodology discussed herein Includes obtaining sensor motion path data at each measurement location pertaining to a candidate implantation site and under candidate pacing settings, as can be understood from FIG. 5 and the associated discussion regarding FIGS. 6A-6D. Once the sensor motion path data is obtained for a measurement location, the sensor motion path data can be normalized and then analyzed with respect to various features or characteristics of the sensor motion path, including total circumference of trajectory or total path length, longest motion vector, eccentricity and hysteresis, as outlined in FIG. 7 and discussed with respect to FIGS. 8A-17. Since the sensor motion path acts as a surrogate for the associated heart tissue motion at the measurement location, the analyzed features or characteristics of the sensor motion path can be assessed to understand which candidate pacing location and associated candidate pacing setting results in the most optimized heart tissue displacement, thereby allowing for optimization of CRT.

Thus, the pacing arrangement (i.e., the combination of candidate implant location and pacing setting at that candidate implant location) that results in the best motion parameters (e.g. path length, vector length, eccentricity, hysteresis) for sensor motion paths as sensed via the MPS sensor at one or more measurement locations during the pacing arrangement may be selected as the optimized CRT pacing arrangement. In the case where the CRT optimization only involves MPS sensor motion measurements at a single measurement location, the selection of optimized CRT pacing arrangement easily follows as the pacing setting that results in the "best" parameter(s) (e.g. path length, vector length, eccentricity, hysteresis) as measured at that single measurement location.

However, if multiple sequential measurement locations are employed as part of the CRT optimization (i.e. test/record a plurality of pacing settings at a first measurement location, then move the MPS sensor to a second measurement location and test/record the plurality of pacing settings, then repeat at a third measurement location and so forth), then either a composite score, a voting scheme, or other means of selecting the best pacing settings may be used to work with evaluating the motion parameters taken at the various measurement locations to determine the optimized CRT pacing arrangement.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A method of optimizing CRT for an implantable pulse generator wherein candidate pacing settings are administered at a candidate lead implantation site, the method comprising:
   determining at least one parameter of a navigation sensor path at a measurement site for each candidate pacing setting at the candidate lead implantation site, wherein x-y-z position data is used to determine the at least one parameter of the navigation sensor path;
   identifying which navigation sensor path, of those determined for each candidate pacing setting, corresponds to a most efficient cardiac tissue displacement; and
   administering electrotherapy corresponding to the identified navigation sensor path and according to the candidate pacing setting corresponding to the identified navigation sensor path;
   wherein the x-y-z position data associated with the at least one parameter of the navigation sensor path for each candidate pacing setting at the candidate lead implantation site is normalized by comparison to a baseline candidate pacing setting; and
   wherein the baseline candidate pacing setting comprises AAI.

2. The method of claim 1, wherein at least one of the candidate pacing settings is administered with different AVD.

3. The method of claim 1, wherein the at least one parameter includes eccentricity.

4. The method of claim 3, wherein an eccentricity of the identified navigation sensor path is closer to a value of one than an eccentricity of any other of the determined navigation sensor paths.

5. The method of claim 1, wherein the at least one parameter of the navigation sensor path is tracked via a navigation sensor located in a low-power magnetic field, the navigation sensor employing a coil.

6. The method of claim 1, wherein the candidate lead implantation site is associated with a LV, and each candidate pacing setting is associated with LV pacing.

7. A method of optimizing CRT for an implantable pulse generator wherein candidate pacing settings are administered at a candidate lead implantation site, the method comprising:
  determining at least one parameter of a navigation sensor path at a measurement site for each candidate pacing setting at the candidate lead implantation site, wherein x-y-z position data is used to determine the at least one parameter of the navigation sensor path;
  identifying which navigation sensor path, of those determined for each candidate pacing setting, corresponds to a most efficient cardiac tissue displacement; and
  administering electrotherapy corresponding to the identified navigation sensor path and according to the candidate pacing setting corresponding to the identified navigation sensor path;
  wherein the at least one parameter includes hysteresis; and
  wherein a first hysteresis component of the identified navigation sensor path is less than a value of $\pi/2$ and also less than a first hysteresis component of any other of the determined navigation sensor paths.

8. The method of claim 7, wherein the first hysteresis component is an area divided by a longest motion vector of the identified navigation sensor path, the area being enclosed by a total circumference of trajectory of the identified navigation sensor path.

9. The method of claim 7, wherein e second hysteresis component of the identified navigation sensor path is greater than a value of one and also greater than a second hysteresis component of any other of the determined navigation sensor paths.

10. The method of claim 9, wherein the second hysteresis component is a diastolic portion of an area divided by a systolic portion of the area, the area being enclosed by a total circumference of trajectory of the identified navigation sensor path.

11. A method of optimizing CRT for an implantable pulse generator wherein candidate pacing settings are administered at a candidate lead implantation site, the method comprising:
  determining at least one parameter of a navigation sensor path at a measurement site for each candidate pacing setting at the candidate lead implantation site, wherein x-y-z position data is used to determine the at least one parameter of the navigation sensor path;
  identifying which navigation sensor path, of those determined for each candidate pacing setting, corresponds to a most efficient cardiac tissue displacement; and
  administering electrotherapy corresponding to the identified navigation sensor path and according to the candidate pacing setting corresponding to the identified navigation sensor path;
  wherein the at least one parameter includes a total circumference of trajectory.

12. A method of optimizing CRT for an implantable pulse generator wherein candidate pacing settings are administered at a candidate lead implantation site, the method comprising:
  determining at least one parameter of a navigation sensor path at a measurement site for each candidate pacing setting at the candidate lead implantation site, wherein x-y-z position data is used to determine the at least one parameter of the navigation sensor path;
  identifying which navigation sensor path, of those determined for each candidate pacing setting, corresponds to a most efficient cardiac tissue displacement; and
  administering electrotherapy corresponding to the identified navigation sensor path and according to the candidate pacing setting corresponding to the identified navigation sensor path;
  wherein the at least one parameter includes a longest motion vector.

13. A system for optimizing CRT when candidate pacing settings are administered at a candidate lead implantation site in a portion of a patient heart, the system comprising:
  a device comprising a navigation sensor at a distal end of the device, the device configured to be delivered intravascular to the portion of the patient heart;
  a tracking system configured to record x-y-z positions of the navigation sensor in a three dimensional x-y-z coordinate system during administration of candidate pacing settings at the candidate lead implantation site; and
  a processor that determines from the recorded x-y-z positions a navigation sensor path for each candidate pacing setting at the candidate lead implantation site;
  wherein the x-y-z position data associated with the navigation sensor path for each candidate pacing setting at the candidate lead implantation site is normalized by comparison to a baseline candidate pacing setting; and
  wherein the baseline candidate acing setting comprises AAI.

14. The system of claim 13, further comprising a display that depicts the navigation sensor path.

* * * * *